(12) United States Patent
Goldenberg (10) Patent No.: US 7,608,048 B2
(45) Date of Patent: *Oct. 27, 2009

(54) ROTATING SOFT TISSUE BIOPSY NEEDLE

(76) Inventor: Alec S. Goldenberg, 157 E. 32nd St., Second Floor, New York, NY (US) 10016

( * ) Notice: Subject to any disclaimer, the term of this patent is extended or adjusted under 35 U.S.C. 154(b) by 728 days.

This patent is subject to a terminal disclaimer.

(21) Appl. No.: 10/901,896

(22) Filed: Jul. 29, 2004

(65) Prior Publication Data

US 2005/0054947 A1     Mar. 10, 2005

Related U.S. Application Data

(60) Provisional application No. 60/498,417, filed on Aug. 28, 2003.

(51) Int. Cl.
*A61B 10/00*     (2006.01)
(52) U.S. Cl. ...................................................... 600/564
(58) Field of Classification Search ................ 600/567, 600/562, 564, 566; 606/167, 170
See application file for complete search history.

(56) References Cited

U.S. PATENT DOCUMENTS 5,617,874 A * 4/1997 Baran ......................... 600/558
6,015,391 A * 1/2000 Rishton et al. ............... 600/567

* cited by examiner

*Primary Examiner*—Max Hindenburg
*Assistant Examiner*—Fangemonique Smith
(74) *Attorney, Agent, or Firm*—Leason Ellis LLP (57) ABSTRACT

In one embodiment, a biopsy needle that is particularly suited for shearing and collecting soft tissue specimens is provided and is formed of an inner tube with a snare at a distal end thereof, an outer cannula, a stylet and a handle assembly. In one aspect of the present invention, the handle assembly includes a spring loaded mechanism described in greater detail below that permits the user to selectively actuate the biopsy needle so that the outer cannula and the inner tube are rapidly advanced beyond the stylet to provide a shearing action of the soft tissue specimen. In one exemplary embodiment, the rapid advancement of the needle to achieve appropriate shear/cutting forces and to facilitate specimen transit into the needle is accomplished by a first spring loaded mechanism. A second spring loaded mechanism is automatically actuated after actuation of the first spring loaded mechanism and serves to rotate the inner tube relative to the outer cannula resulting in actuation of the snare coil.

18 Claims, 8 Drawing Sheets

ROTATING SOFT TISSUE BIOPSY NEEDLE

CROSS-REFERENCE TO RELATED APPLICATION

This application claims the benefit of U.S. patent application Ser. No. 60/498,417, filed Aug. 28, 2003, which is hereby incorporated by reference in its entirety.

TECHNICAL FIELD

The present invention relates to a surgical instrument, typically known as a biopsy needle or cannula that is used to gather tissue from living persons or animals for pathological study and more particularly, relates to a rotating biopsy needle having an improved structure for severing a soft tissue sample and/or retaining the tissue sample within the biopsy needle.

BACKGROUND

For various medical reasons, such as diagnostic tests or the like, it is often necessary for a physician to obtain a sample of a patient's body. Often, it is required for the physician to take a sample from a soft tissue such as a breast biopsy specimen as opposed to a more rigid structure, such as a bone marrow specimen. Soft tissue specimens generally contain a less rigid structure and are by definition "soft" or easily deformable as opposed to bone marrow structures which are recovered with significant portions of their internal bony trabecular structure intact.

One exemplary surgical instrument for the severing and/or retrieval of biopsy specimens is disclosed in U.S. Pat. Nos. 5,522,398; 5843,001; and 6,015,391, of which the present applicant is also inventor. Each of these patents is hereby expressly incorporated herein by reference. While these instruments are particularly suited for severing and collecting a more rigid tissue specimen, such as a bone marrow specimen, the instruments are not as effective at severing and/or retaining soft tissue samples. In addition, the concept of recovering a specimen by pushing it toward the handle from the tip of the needle may not be as applicable for soft tissue specimens as it is for bone marrow specimens. An attempt to push the specimen through the needle can result in disruption of the specimen because soft tissue specimens have less structure. Moreover in a long needle, such as an endoscopic SNARECOIL (trademark) needle, the length of the needle would be prohibitive in successfully pushing the specimen out of the proximal end of the needle and recovering an intact sample.

Other conventional procedures and instruments used for obtaining the samples, while not overly complex, almost universally result in excessive patient discomfort and often overly extends the patient's and operator's time and money.

SUMMARY

In one embodiment, a biopsy needle that is particularly suited for shearing and collecting soft tissue specimens is provided and is formed of an inner tube with a snare at a distal end thereof, an outer cannula, a stylet and a handle assembly. In one aspect of the present invention, the handle assembly includes a first biasing mechanism described in greater detail below that permits the user to selectively actuate the biopsy needle so that the outer cannula and the inner tube are rapidly advanced beyond the stylet to provide a shearing action of the soft tissue specimen. The biopsy needle also includes a second biasing mechanism that automatically actuates subsequent to the actuation of the first biasing mechanism and serves to rotate the inner tube relative to the outer cannula to actuate the snare coil in a staged manner. In other words, the needle is of a rotating type in that in one embodiment, a cannula (outer cannula) is connected to a sleeve with a pin and groove mechanism that causes it to rotate as it is rapidly advanced.

In another aspect of the present invention, a three cannula needle is provided and includes a third retractable cannula that can be selectively retracted over the outer cannula so as to expose a specimen that is sitting in the innermost member, namely, the inner tube. More specifically, each of the inner tube and the outer cannula has a cut away portion (window) that are both in registration with one another after the outer cannula and inner tube have been axially projected and rotated to an end position where the specimen has been sheared and captured within the inner tube. To expose the aligned windows, the third outer most retractable cannula is simply moved back and the user can easily recover the specimen that is resting within the cradle of the inner tube. This facilitates removal of the specimen.

Other features and advantages of the present invention will be apparent from the following detailed description when read in conjunction with the accompanying drawings.

BRIEF DESCRIPTION OF THE DRAWING FIGURES

The foregoing and other features of the present invention will be more readily apparent from the following detailed description and drawings figures of illustrative embodiments of the invention in which.

DETAILED DESCRIPTION OF PREFERRED EMBODIMENTS

Referring now to FIGS. 1-11, a biopsy needle 100 according to one exemplary embodiment is illustrated. The biopsy needle 100 includes an inner tube 110 with a snare 300 at a distal end thereof, an outer cannula 120, a stylet 310 and a handle assembly 400. In one aspect of the present invention, the handle assembly 400 includes a biasing (spring loaded) mechanism described in greater detail below that permits the user to selectively actuate the biopsy needle 100 so that the outer cannula 120 and the inner tube 110 are rapidly advanced beyond the stylet 310 to provide a shearing action of the soft tissue specimen.

Figure 1:
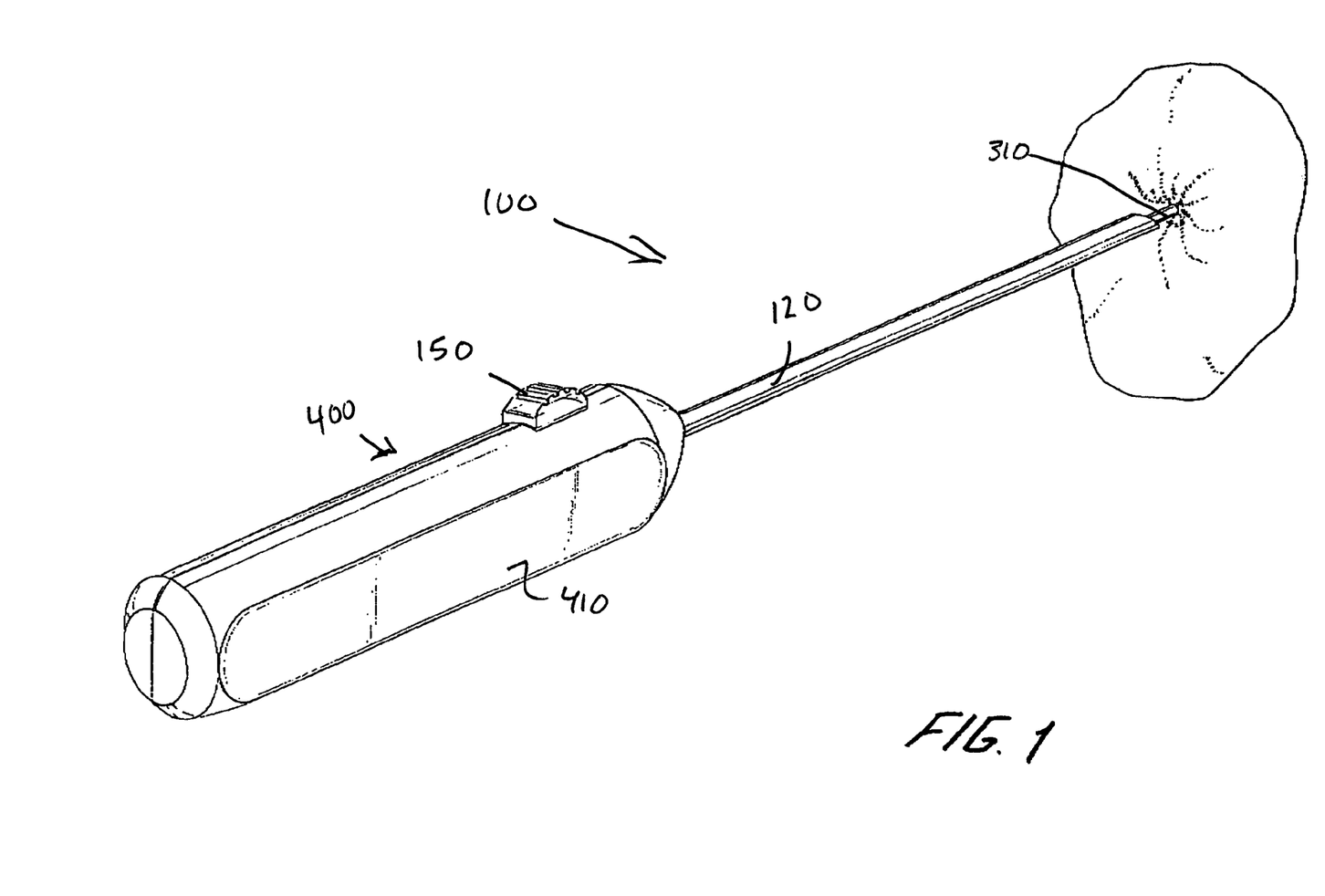
FIG. 1 is a perspective view of a biopsy needle according to a first embodiment.

The present biopsy needle 100 is constructed for soft biopsy applications since the spring loaded mechanism provides an improved means of removing the tissue after it is cored as well as providing an improvement in the way that the tissue is acquired by the needle 100. The handle assembly 400 includes a handle body 410 that can be formed in number of different shapes and sizes and is generally a hollow body that contains the spring loaded mechanism. For purpose of illustration only, the handle body 410 of FIG. 1 is a generally rectangular or square body; however, handle body 410 preferably is an ergonomically pleasing shape. The handle body 410 includes an opening 412 that permits a portion of a first mechanical mechanism to extend therethrough so as to be accessible by the user as is described in greater detail below.

The inner tube 110 is preferably similar or identical to the inner tube disclosed in one of the aforementioned patents. More specifically, the inner tube 110 includes a distal end and an opposing proximal end 114. The inner tube 110 can have any number of different cross-sectional shapes; however, in one embodiment, the inner tube 110 has a circular cross-section. The inner tube 110 includes a flange 116 that is spaced from the proximal end 114 and extends outwardly from the inner tube 110. The flange 116 can be in the form of an annular flange that extends completely around the inner tube 110 or it can be in the form of one or more protrusions, e.g., tabs, that extend outward from the inner tube 110. In the illustrated embodiment, the flange 116 is in the form of an annular ring with a pair of integral tabs (ears) 117 formed as part of the flange 116 and extending outwardly therefrom. The pair of tabs 117 are spaced apart from one another and preferably, the tabs 117 are spaced about 180 degrees apart from one another and the outer sections of the tabs 117 have curved surfaces.

The outer cannula 120 is preferably similar or identical to the outer tube disclosed in one of the aforementioned patents. More specifically, the outer cannula 120 includes a distal end and an opposing proximal end 124. The outer cannula 120 can also have any number of different cross-sectional shapes with one embodiment being a circular tube structure. At the proximal end 124 of the outer cannula 120, a flange 126 is formed. As with the flange 116, the flange 126 can be in the form of an annular flange or it can be formed by one or more protrusions or tabs. The outer cannula 120 also has a pair of tabs or ears 128 formed as a part thereof. As with the inner tube 110, the pair of tabs 128 are spaced apart from one another and preferably, the pair of tabs 128 are spaced apart about 180 degrees.

Before proceeding to an explanation of the other operable components of the spring loaded mechanism, it is helpful to understand that generally the inner tube 110 and outer cannula 120 are positionable between two positions, namely, a fully retracted position and a fully extended position. In the fully retracted position, the inner tube 110 and outer cannula 120 are reset back into the handle body 410 and a biasing element(s) of the spring loaded mechanism stores energy. In contrast, after the user activates the spring loaded mechanism, the biasing element releases its energy and an axial force is applied to the inner and outer tube structure in a direction away from the handle body 410.

In both the fully retracted and fully extended positions, the flange members 116, 126 are coupled to one another, as described below, so that a force applied to one of the inner tube 110 and the outer cannula 120 is translated to the other of the inner tube 110 and outer cannula 120.

Figure 3:
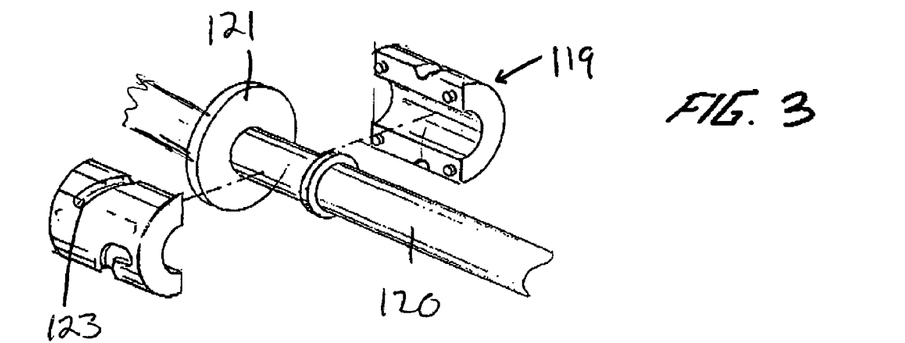
FIG. 3 is an exploded perspective view, in partial cross-section, of a rotating sleeve that is disposed about a length of an outer cannula of the needle.

In order to generate a force that is sufficient to shear the soft tissue, the spring loaded mechanism includes a first biasing element 130, such as a coil spring, that applies a force against a face of an outer sleeve 119 that is disposed around and connected to the outer cannula 120 as shown in FIG. 3. More specifically, the outer sleeve 119 has a first end at which a flange member 121 is formed and a body section 122 which in the illustrated embodiment is a tubular structure. The outer sleeve 119 is directly attached to the outer cannula 120 so that movement of one of the members is directly translated to the same type of movement of the other of the members. The outer sleeve 119 has a groove 123 formed therein and in one embodiment, the groove 123 has a spiral or helical shape. The sleeve 119 can have two grooves and as used herein, the term groove refers to either a recessed channel formed in a body or a slot or opening that is formed completely through the body. In addition, one will appreciate that other pin and groove arrangements can be provided as a means for rotating the outer cannula 120. For example, other designs are possible including symmetrical placement of pins on both sides of the sleeve which engage complementary grooves in the sleeve and can lead to a more efficient and stable translation of the axial motion into a rotation of the cannula. In addition, it will be appreciated that the groove 123 can be formed in the outer cannula 120 itself, thus eliminating the need for the sleeve 119.

One or more pins or projections 127 are received within the groove 123 with the pin 127 being fixed relative to the handle body 410. More specifically, each pin 127 is securely attached to the handle body 410 and is sized so that it at least partially extends into the groove 123. In other words, it is sufficient for the pin 127 to be a small projection coupled to housing 410 which extends into the groove 123. One will appreciate that this is a pin in groove arrangement and therefore, when the outer cannula/outer sleeve is advanced, the pin 127 travels within the groove 123 and the helical nature of the groove 123 causes the outer cannula/outer sleeve to rotate as the outer cannula 120 continues to advance axially in the longitudinal direction.

The first biasing element 130 is contained within the handle body 410 by being disposed between the flange 121 and an interference member 140 that is formed as part of the handle body 410 such that the outer cannula 120 can freely travel therethrough in a sliding manner, while the first biasing element 130 is external to the outer cannula 120. More specifically, the interference member 140 can be in the form of an annular flange that has an opening formed therethrough to accommodate the outer cannula 120. The interference member 140 is thus fixed relative to the handle 400 and relative to the movable inner tube 110 and outer cannula 120.

The spring loaded mechanism includes an operable actuator device 150 that causes the release of the first biasing element 130 from its compressed state, thereby resulting in the first biasing element 130 releasing at least some of its stored energy. One exemplary actuator device 150 is a pivotable lever that at least partially extends through an opening 413 formed in the handle body 410. The device 150 has a button or the like 152 which the user manipulates to cause the pivoting of the device 150 and release of the first biasing element 130. The button 152 is disposed along an outer surface of the handle body 410. The device 150 is formed of an elongated finger or post 154 that has the button 152 attached or formed at one end and terminates at the other end in a claw or tab 15 that is provided to engage the annular flange 116 and lock the inner and outer tubes 110, 120 in the retracted position. The device 150 includes a biasing element, such as a spring, 158 that is attached at one end to the housing and at its other end to the post 154 which applies a biasing force to the post 154, thereby biasing the post 154 in a manner such that it engages and applies a force against the flange 116 when the device 150 is in a closed position. As the user slides the button 152, the biasing force of the spring 158 is overcome and the device 150 pivots about the post 154 in a direction where the claw 156 clears the flange 116, thereby releasing the inner tube 110 for axial movement.

As previously mentioned, the first biasing element 130 applies a biasing force against one face of the flange member 121 and since the outer sleeve 119 is directly connected to the outer cannula 120, the first biasing element 130 likewise applies a force to the outer cannula 120. When the claw 156 seats against the flange 121 it acts to lock the outer sleeve/outer cannula in the retracted position since it prevents any axial movement of the outer cannula 120 or sleeve 119, which is frictional fit or otherwise securely attached to the outer cannula 120, in a direction away from the handle body 410.

As soon as the claw 156 becomes disengaged from the flange 116, the first biasing element 130 releases its stored energy by applying a force against the flange 121. This release of energy results in axial movement of the outer cannula 120 and sleeve 119 as sequentially shown in FIGS. 6-8. The sleeve 119 limits the degree of travel of the outer cannula 120 since the sleeve 119 has dimensions greater than the dimensions of the opening in the handle body 410 through which the outer cannula 120 extends. In the fully extended position, the sleeve 119 seats against the handle body 410 with the first biasing element 130 being in a more elongated condition, released of its stored energy.

It will also be appreciated that an opposite arrangement that achieves the same result can be provided, namely, one in which the outer cannula 120 has one or more projections that travel in a helical groove associated with the housing. Thus, after the flange 121 is disengages, the outer cannula 120 moves axially forward and also begins to rotate since the pin or projections that are part of the cannula 120 ride within the helical groove, so as to cause rotation of the outer cannula as it is axially advanced.

The first stage which is defined by the release and axial driving of the outer tube 120 can be characterized as being a torque generating mechanism having a first component and a second component with one component being fixed in the longitudinal axial direction, while the other component is movable in the axial direction. One of the components is associated with the outer cannula, while the other component is associated with another part of the needle. Thus, in one embodiment, the component associated with the outer cannula moves axially and mates with the other component which is fixed axially to cause rotation of the outer cannula as it advances. In another embodiment, the components associated with the outer cannula does not move axially and mates with the other component that does move axially, thereby causing rotation of the outer cannula 120 as it advances.

In the illustrated embodiment, as the outer sleeve 119 is biased forward due to the first biasing element 130 releasing its energy, the one or more fixed pins 127 control the manner in which the outer sleeve 119 moves axially forward. More specifically, the helical nature of the groove 123 causes the outer sleeve 119 to begin to rotate as it is advanced axially forward. Since the outer sleeve 119 is directly connected to the outer cannula 120, the rotation of the outer sleeve 119 is directly translated into rotation of the outer cannula 120.

Preferably, an alignment sleeve 160 is provided and is disposed around a portion of the inner tube 110 and outer cannula 120. The alignment sleeve 160 is disclosed within the housing body 410 and is a generally hollow structure such that the outer cannula 120 and the inner tube 110 are received therethrough. In one embodiment, the alignment sleeve 160 is a generally annular structure with a flange 162 formed as part thereof and extending outwardly from an outer surface 164 of the sleeve 160. The flange 162 is thus a radial flange that extends around the sleeve 160 and serves to restrict the axial movement of the sleeve 160, while permitting the sleeve 160 to rotate. More specifically, the flange 162 is received within a complementary groove or channel (not shown) or other retaining structure which is formed in the body 410. By disposing the flange 162 in a complementary groove, the alignment sleeve 160 is permitted to rotate therein; however, it can not move axially forward in the housing.

Figure 2:
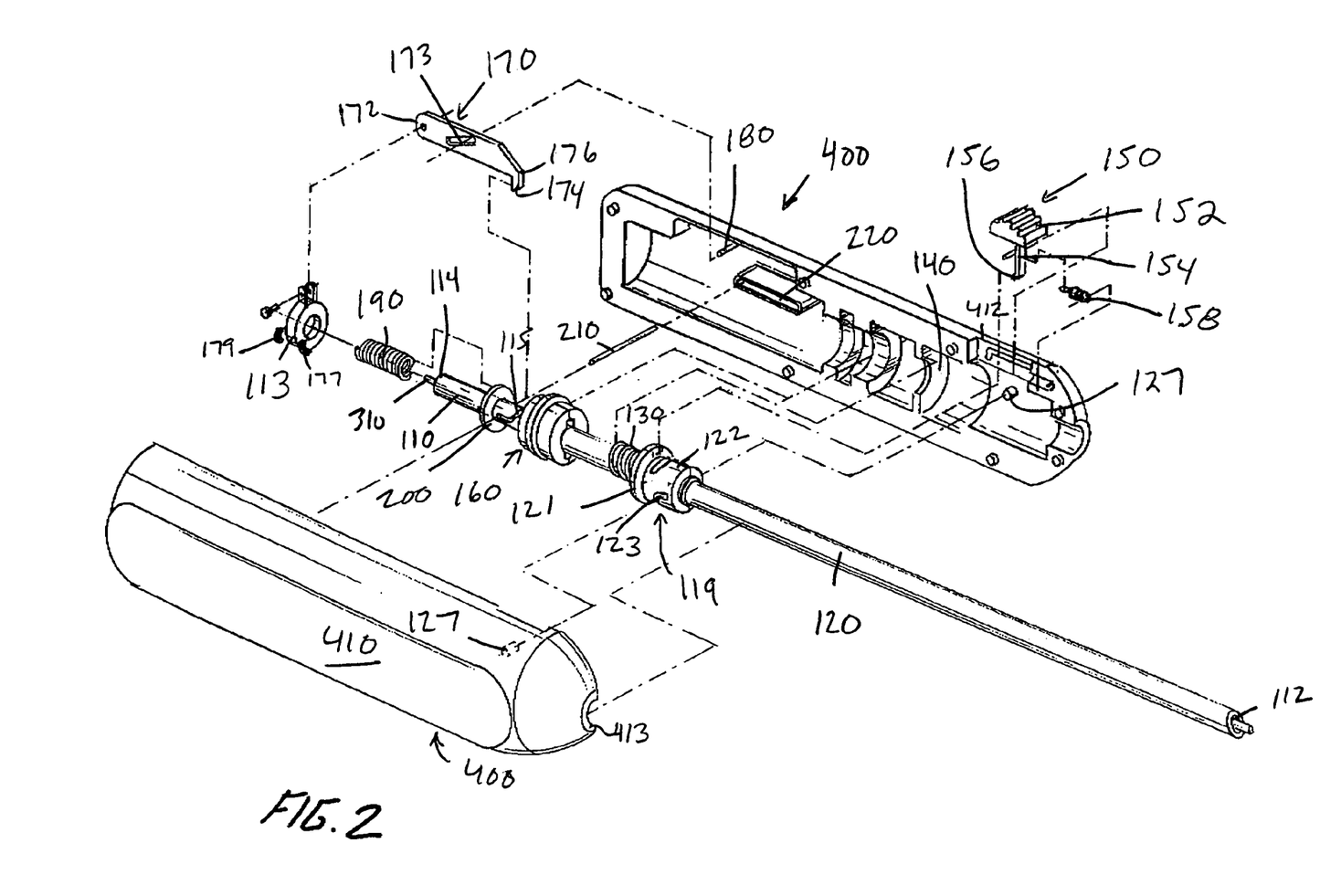
FIG. 2 is an exploded perspective view of the needle of FIG. 1.
Figure 4:
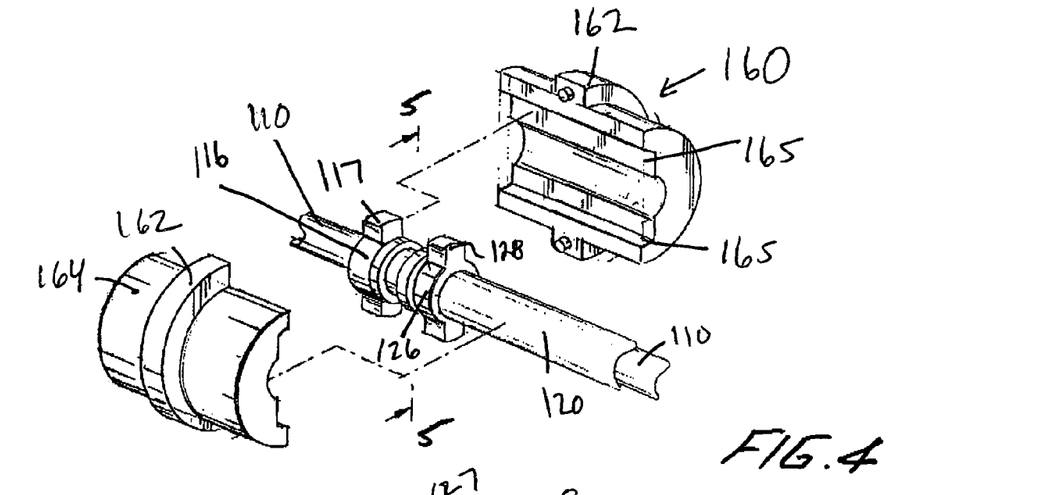
FIG. 4 is an exploded perspective view, in partial cross-section, of an alignment sleeve of the needle of FIG. 1.

The alignment sleeve 160 also has features formed within the bore extending therethrough to locate and control the movement of the inner tube 110 and the outer cannula 120. As best shown in FIGS. 2 and 4, the alignment sleeve 160 has a pair of grooves or channel 165 formed within an inside thereof. The grooves 165 are constructed to receive the tabs 117, 128 of the flanges 116, 126 of the inner tube 110 and the outer cannula 120, respectively, and therefore, the grooves 165 are spaced apart from one another in the same manner as the tabs 117, 128 of each of the inner tube 110 and outer cannula 120 are spaced apart. In the illustrated embodiment, the grooves 165 are thus spaced about 180 degrees apart from one another. The grooves 165 have a complementary arcuate shape (e.g., semi-circular) so as to receive the tabs 117, 128 which themselves are semi-circular. The grooves 165 extend from one end to the other end of the alignment sleeve 160.

Since the grooves 165 have a complementary shape as the tabs 117, 128, the inner tube 110 and the outer cannula 120 are permitted to move axially within the alignment sleeve 160; however, the two are not permitted to rotate independent from one another. Instead, the inner tube 110 and outer cannula 120 rotate together when the alignment sleeve 160 itself rotates. As previously mentioned, the alignment sleeve 160 does not move axially within the handle body 410 but rather is only permitted to rotate and thus, the rotation of the alignment sleeve 160 is directly translated into rotation of the inner tube 110 and/or the outer cannula 120.

Figure 5:
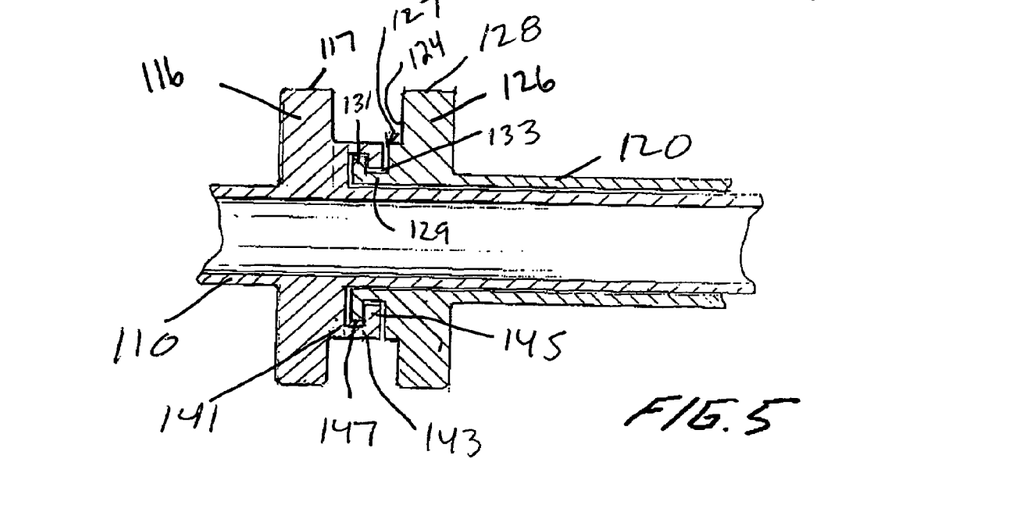
FIG. 5 is a cross-sectional view taken along the line 5-5 of FIG. 4.
Figure 6:
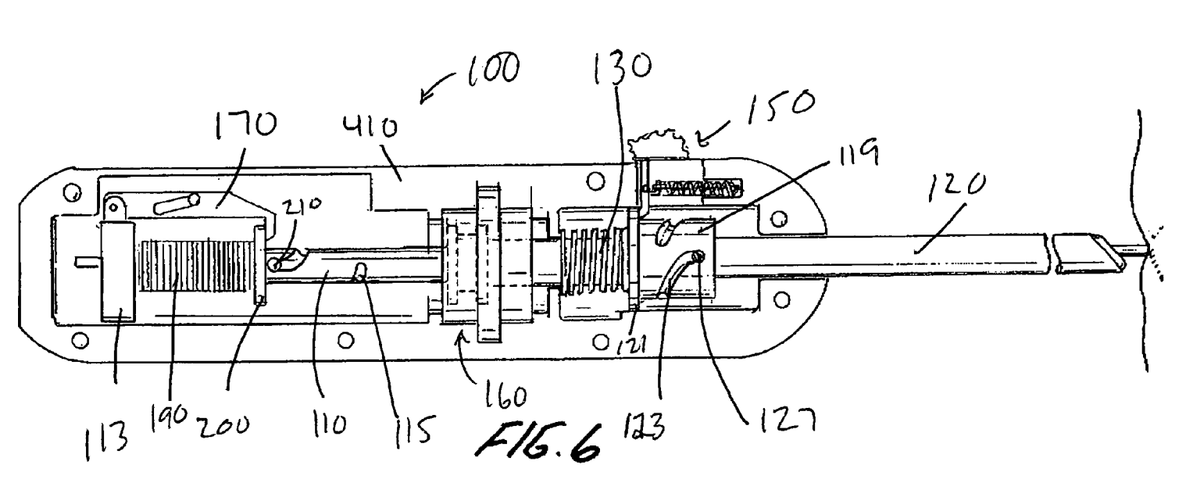
FIG. 6 is a cross-sectional elevation view of the needle of FIG. 1 in a rest position.
Figure 7:
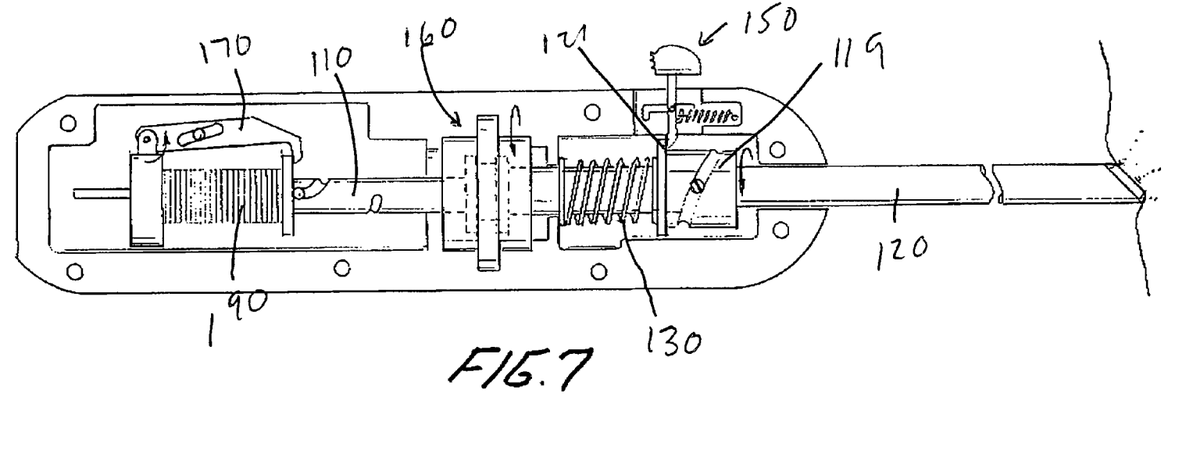
FIG. 7 is a cross-sectional elevation view of the needle of FIG. 1 at an intermediate position of a first stage.
Figure 8:
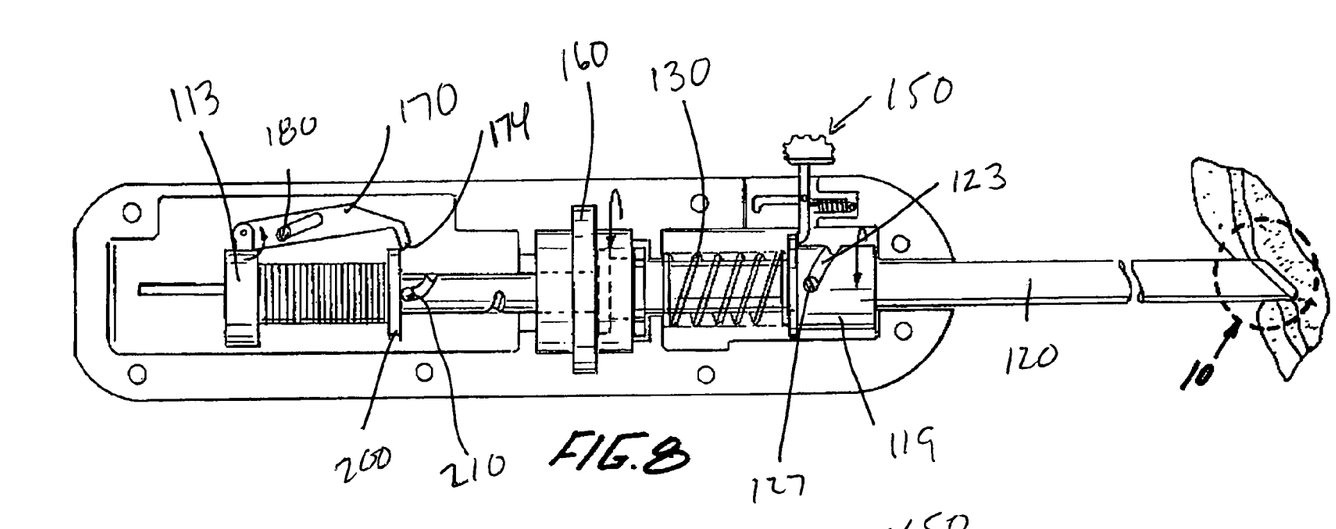
FIG. 8 is a cross-sectional elevation view of the needle of FIG. 1 shown at the completion of the first stage.
Figure 9:
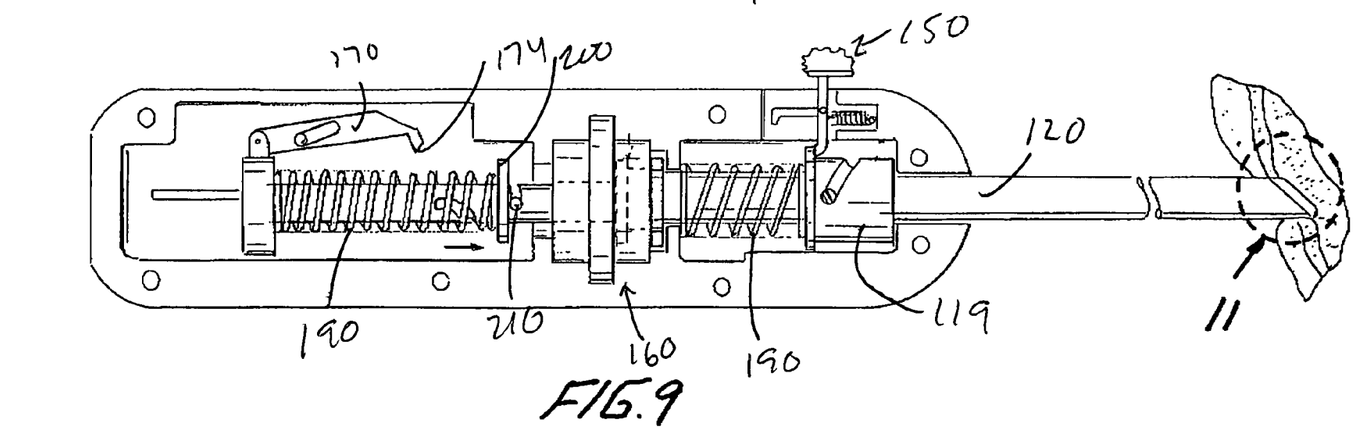
FIG. 9 is a cross-sectional elevation view of the needle of FIG. 1 shown at the completion of a second stage.
Figure 10:
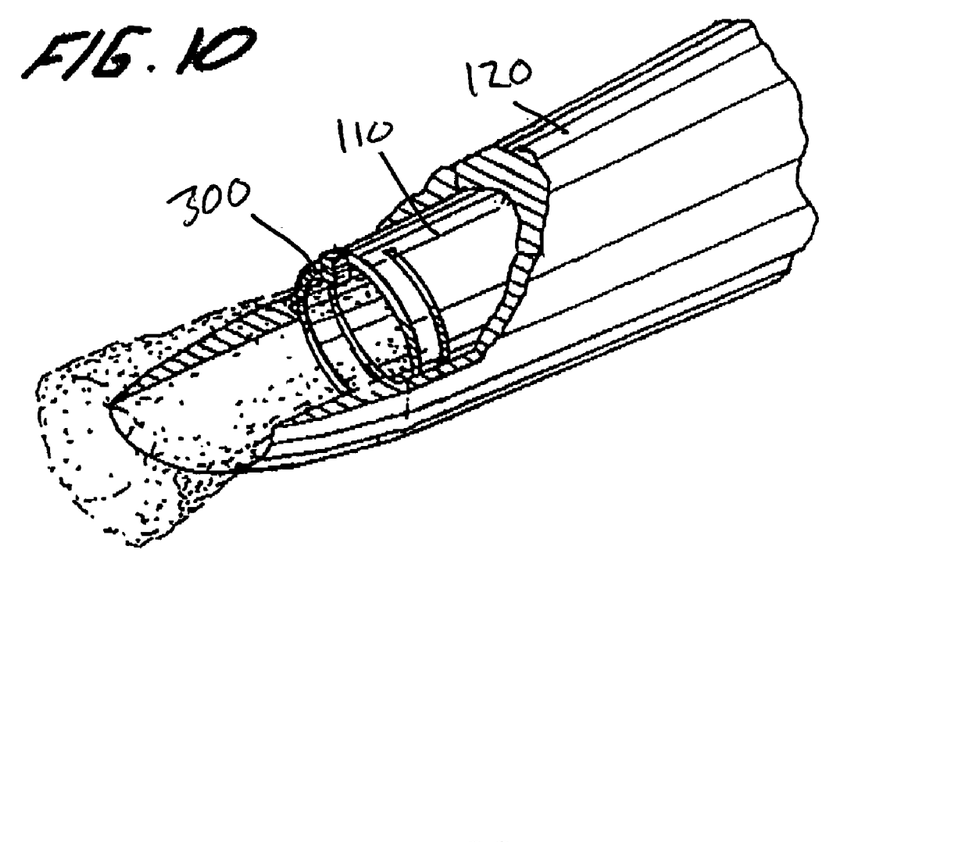
FIG. 10 is an enlarged sectional view taken around the circle of FIG. 8.
Figure 11:
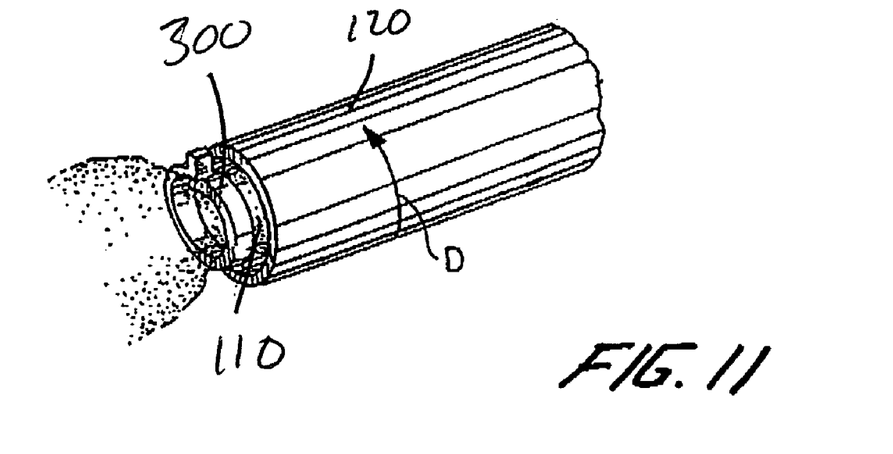
FIG. 11 is an enlarged sectional view taken around the circle of FIG. 9.

FIG. 5 is an enlarged sectional view of the interaction and coupling between the inner tube 110 and the outer cannula 120. More specifically, the flange 126 at the proximal end of the outer cannula 120 includes a first locking lip 127 and the flange 116 at the proximal end of the inner tube 110 includes a second locking lip 141 that is complementary to the first locking lip 127 such that the two interlock with one another. The first locking lip 127 is formed on one face of the flange 126 and the second locking lip 141 is formed on the face of the flange 116 that faces the flange 126. The first locking lip 127 can be annular in shape or it can be formed as one or more spaced lip segments so long as there are complementary lip segments formed on the opposing second locking lip 141. The first locking lip 127 has a portion 129 that is perpendicular to the flange 126 such that it extends outwardly therefrom and the portion 129 terminates in a lip portion 131. A space 133 is formed between the lip portion 131 and the flange 126. Similarly, the second locking lip 141 has a portion 143 that is perpendicular to the flange 116 such that it extends outwardly therefrom toward the flange 126 and the portion 143 terminates in a lip portion 145. A space 147 is formed between the lip portion 145 and the flange 116. To couple the inner tube 110 to the outer cannula 120, the lip portion 131 of the first locking lip 127 is disposed within the space 147 and the lip portion 145 is received within the space 133. In this manner, the lip portions 131, 145 interlock with one another and prevent independent axial movement between the inner tube 110 and the outer cannula 120. FIG. 4 also illustrates the tabs 117 of the flange 116 and the tabs 128 formed as part of the flange 126.

It will be appreciated that the alignment sleeve 160 causes the inner tube 110 to rotate since it is directly coupled to the outer cannula 120 which can be set into rotation by actuation of the device 150 as described hereinbefore. In other words, initial rotation of the outer cannula is translated to rotation of the sleeve 119 and the inner tube 110. More specifically, the pin and groove construction of the sleeve 119 and the direct connection between the sleeve 119 and the outer cannula 120 causes the rotation of the outer cannula 120 upon actuation of the device 150 and because the inner tube 110 is captured within grooves 165 of the alignment sleeve 160 as with the outer cannula 120, the rotation of the outer cannula 120 is translated to rotation of the alignment sleeve 160 which in turn translates rotation to the inner tube 110. It will be appreciated that the locking between the flanges 116, 126 causes the inner tube 110 and the outer cannula 120 to move axially together while both are rotating.

The spring loaded mechanism has another component thereof in that it generally includes a pin and groove arrangement to control the specific movements of the inner tube 110 as it is fired and advanced away from the handle body 410 upon actuation of the spring loaded mechanism. For example, the end 114 of the inner tube 110 has a flange member 113 which can be an annular flange or can be less than an annular flange. The end 114 (flange 113 thereof) thus has an opening formed thereat to permit the stylet 310 to be received and removed therethrough.

It will be appreciated that the inner tube 110 should be able to rotate within the flange 113 and therefore, it is preferred that the flange 113 be connected to the inner tube 110 in a non-movable manner so as to permit the inner tube 110 to rotate when it axially advances as will be described hereinafter. For example and as shown in FIG. 1, first and second locator members 177, 179 are disposed around the flange 113 so as to locate the flange 113 and limit the movement thereof. More specifically, the first locator member 177 is in the form of a distal flange (e.g., ring shaped) and the second locator member 179 (e.g., ring shaped) is in the form of a proximal flange. These flanges 177, 179 prevents flange 113 from translating along an axial (longitudinal) direction relative to the inner tube 110 but allows the inner tube 110 to freely rotate within the flange 113.

A second pivotable lever 170 is provided and is pivotally connected to the flange 113 formed at the end of the inner tube 110. The lever 170 is preferably pivotally connected to the flange 113 at a first end 172 and has a claw or lip 174 formed at an opposing second end 176. The illustrated claw 174 is a protrusion that is generally perpendicular to the elongated body portion of the lever 170. The lever 170 includes an opening 173 formed therethrough to receive a pin or the like 180. In one aspect of the illustrated spring loaded mechanism, the opening 173 is a slot that is formed at an angle within the lever body and more specifically, the slot 173 is angled upward in a direction toward the claw 174. In the retracted, locked position of the spring loaded mechanism, the pin 180 is disposed within the slot 173 near or at the end that is closest to the claw 174 and after activation of the first lever mechanism (actuator device 150), the pin 180 rides within the slot 173 toward the opposite end thereof causing the disengagement of the second pivotable lever 170 as will be described in greater detail hereinafter.

The illustrated pin and groove mechanism includes a second biasing element 190 that is disposed between the flange 113 or locator member 177 and a movable member 200 that is disposed around the inner tube 110. The member 200 is free to slidably travel along the inner tube 110 when it is unlocked from the claw 174 of the lever 170. The member 200 thus has an opening extending therethrough that accommodates the inner tube 110 and has a first face that faces and is in contact with the second biasing element 190 and a second face that faces the alignment sleeve 160. In one exemplary embodiment, the member 200 is generally in the form of a ring shaped member. The member 200 has a surface that can be engaged by the claw 174 so as to keep the second lever mechanism in a locked position. In the locked position, the second biasing element 190 is in a compressed state (storing energy) between the first face and the distal locator member 177 that is adjacent the flange 113.

According to the illustrated embodiment, the pin and groove mechanism associated with the second pivotable lever 170 is formed of a pin 210 and the inner tube 110 has one or more complementary profiled grooves 115 formed therein. In the illustrated embodiment, each groove 115 can have a first generally linear portion and a second portion that is generally helical in nature.

The pin 210 is contained within the handle body 410 such that it has two different stages of movement in that the pin 210 is initially permitted to rotate with the inner tube 110 and then in a second stage, the pin 210 moves forward in a single plane. More specifically, the pin 210 is directly coupled to the member 200 by any number of means such that movement of the inner tube 110 is directly translated to movement of the member 200 and the pin 210. For example, the pin 210 can be integrally formed with the member 200 so that it extends across a diameter thereof or the pin 210 can be securely attached to the member 200 using any number of means. For example, a pair of fastening members 211 can be formed as part of the member 200 at locations about 180 degrees apart from one another. Each member 211 can be generally in the form of a bridge that has a space formed therethrough to receive the pin 210 so as to securely attach the pin 210 to the member 200. Any other means can be used to attach the two together.

Initially in the first stage of movement, the pin 210 travels within the groove 115 as it rotates along with the inner tube 110. In other words, as the inner tube 110 rotates, the member 200 and the pin 210 also rotate and then, in the second stage, the pin 210 moves forward in a single plane as it is advanced within the one or more grooves 115. In other words, the pin 210 does not have an up and down movement as it advances but rather it remains substantially within one plane. This type of movement by the pin 210 is created by disposing the ends of the pin 210 within longitudinal channels 220 that are formed in the handle body 410 on opposite sides of the inner tube 110. The channels 220 are aligned with one another so that they lie within one plane that also contains the pin 210 during its travel in the second stage. One end of the channel 220 is open so as to be able to receive the pin 210.

As will be appreciated, the inner tube 110 rotates as the inner tube 110 and the outer cannula 120 are projected forward while, the alignment sleeve 160 keeps these two members aligned with one another. However, the pin 210 traverses the inner tube 110 perpendicular to the axial dimension. Therefore, the pin 210 should be able to rotate with the inner tube 110 until it engages the channels 220 only after the inner tube 110 has been projected forward. In the present embodiment, the pin 210 does not engage the channels 220 prior to the activation of the biasing element but engages them once the inner tube 110 and the outer cannula 120 have been projected forward. Since the inner tube 110 and the outer cannula 120 rotate a defined number of degrees, the channels 220 can be placed in a position to accept the pin 210 once the rotation is complete.

By directing the ends of the pin 210 into and along the channels 220, the channels 220 act as guide tracks in that they restrict and control the motion of the pin 210 after the unlocking of the second lever mechanism 170 and after the pin 210 has completed its rotation with the inner tube 110. The pin 210 is thus limited to traveling within one plane since as it travels in the second stage, it is restricted to traveling within the linear channels 220.

It will be appreciated that since the stylet 310 does not rotate, the stylet 310 has to accommodate the pin 210. In one embodiment, the stylet 310 remains in the location shown in FIG. 1; however, the pin 210 does not extend completely across the inner tube through the stylet 310 but instead the pin 210 only enters the groove 115 of the inner tube 110 a sufficient degree to rotatably couple the two together while permitting the stylet 310 to remain in a non-rotational state. In other embodiment, the stylet 310 is moved more distally forward in the handle body 410 such that pin 210 can extend completely through the inner tube 110 without any interference with the stylet 310. In other words, the stylet 310 is positioned more distal than the pin slots 220 to allow the pin 210 to rotate with the inner tube 110 as it is advancing axially forward.

Since the pin 210 may not exactly line-up with the channels 220 once the rotation of the inner tube 110 and the outer cannula 120 is complete, the proximal ends of the channels 220 where they accept the pin 210 can be made wider then at the more distal ends of the channels 220 where the pin 210 stops its forward motion. Once, the pin 210 lies within the channels 220, the pin and groove mechanism can be activated (second lever mechanism 170).

It will be appreciated that after the first stage of snare activation in which the outer cannula 120 is advanced and rotated, along with the inner tube 110, the second stage of the activation of the snare preferably occurs once the flange 126 of the outer cannula 120 has cleared the groove 165 and no longer can influence rotation of the alignment sleeve 160. However, it will be appreciated that even when the flange 126 is outside of the sleeve 160, it is still directly attached to the inner tube 110 via the locking lips. In the second stage, the inner tube 110 is rotated, as it remains axially steadfast, due to the activation of the second biasing mechanism and release of stored energy in the second bias element 190. Thus, one will appreciate that preferably at any one point in time, the alignment sleeve is only under the influence and is rotated by either the outer cannula 120 or the inner tube 110. More specifically, in the first stage, the outer cannula 120 causes the alignment sleeve and in the second stage when the flange 126 is free of the alignment sleeve, the release of energy stored in spring 190 causes rotation of the inner tube 110 which is translated into rotational of the alignment sleeve. Even though the inner tube 110 is connected to the outer cannula 120, the locking lips permit the inner tube 110 to rotate relative to the outer cannula in the second stage, while the outer cannula 120 does not have to rotate.

The operation of the device 100 will now be described. In the retracted position, the actuator device 150 and the second pivotable lever 170 are in the locked positions, whereby both the first biasing element 130 and the second biasing element 190 are in compressed states such that they store energy. To actuate the device 100, the user presses, slides or otherwise manipulates the button 152 causing the links 154, 156 to pivot and the claw 159 disengages from the flange 121 of the outer sleeve 119. As soon as the claw 159 disengages, the first biasing element 130 releases its energy by applying a biasing force against the flange 121, which in turn causes the axial (longitudinal) movement of the outer cannula 120. As previously mentioned, the distance that these two elements can axially travel is defined as distance x as illustrated in FIG. 1, namely the distance from the flange 121 to the handle body 410.

The first biasing element 130 is preferably a strong coil spring since this biasing element needs to generate a sufficient force that drives the inner and outer tubes 110, 120 into the tissue so as to shear the soft tissue to permit it to be collected as a result of the action of the snare 300.

The forward axial motion of the outer sleeve 119 is influenced by the pin and groove arrangement in that the groove 123 formed in the outer sleeve 119 and the pin 127 cause the outer sleeve 119 to rotate as it is projected forward. Since the outer sleeve 119 is directly connected to the outer cannula 120, the rotation and forward movement of the outer sleeve 119 is imparted to the outer cannula 120.

As previously mentioned, the outer cannula 120 and inner tube 110 are coupled to one another at their respective flanges 116, 126 by means of the first and second locking lips 127, 141, respectively. Since the outer cannula 120 and inner tube 110 are attached to one another, the rotation of the outer cannula 120 is translated to rotation of the inner tube 110. The alignment sleeve 160 permits the inner tube 110 and the outer cannula 120 to not only continue their forward projection but also it permits these members to rotate uniformly. The tabs 117, 128 of the flanges 116, 126 move axially in the grooves 165 formed in the alignment sleeve 160 until the flange 126 of the outer cannula 120 becomes disengaged from the alignment sleeve. Once the flange 126 becomes disengaged from the alignment sleeve 160 (the tabs 128 clear the groove 165), the outer cannula 120 is free to rotate independent from the inner tube 110, while the two members are still coupled to one another by the first and second locking lips 127, 141.

As soon as the forward motion of the outer cannula 120/ outer sleeve 119 is complete and when the flange 126 of the outer cannula 120 becomes disengaged from the alignment sleeve 160 by sliding out of the grooves 165 thereof, the pin 210 is positioned at the entrance or slightly within the channels 220 and then the second pivotable lever 170 is actuated or fired to cause further rotation of the inner tube 110 to actuate the snare 300. In other words, once the forward projection of the outer cannula 120 is complete and the pin 210 is properly positioned relative to the channels 220, the second pivotable lever 170 fires because the second pivotable lever 170 is connected to the inner tube 110 and therefore it will move along with the inner tube 110 after the actuator device 150 is activated. As the second pivotable lever 170 moves axially with the inner tube 110, the fixed pin 180 rides within the slot 173 toward the opposite end of the slot 173. Because the slot 173 is ramped or angled downward toward this opposite end, the relative movement of the fixed pin 180 within the slot 173 causes the second pivotable lever 170 to pivot upward about the pivot point between the lever 170 and the flange 113. As the lever 170 pivots upward, the claw 174 lifts up from its engagement with the member 200, thereby releasing the member 200 from its locked position. As soon as the member 200 is disengaged from the claw 174, the member 200 is free to move axially (longitudinally) along the inner tube 110 and the second biasing element 190 can release its energy. The second biasing element 190 applies a force against the member 200 in a direction toward the outer cannula 120/alignment sleeve 160.

The pin 210 is placed adjacent and coupled to the member 200 such that when the second biasing element 190 applies a force against the member 200, the force is also translated to the pin 210 causing the pin 210 to ride within the one or more grooves 115 that are formed in the inner tube 110. Because the ends of the pin 210 are constrained within the longitudinal channels 220, the pin 210 can only be advanced within one plane when it is "fired" forward by the biasing force of the second biasing element 190. Because the pin 210 is constrained to one plane, its forward advancement is translated into a rotational movement of the inner tube 110 due to the presence of the profiled helical portion of the groove 115. However, the inner tube 110 is not axially advanced as it rotates. As will be appreciated, the pin 210 advances within the channels 220 but at the same time, the pin 210 advances within the groove 115 from the linear portion to the helical portion. The only way that the pin 210 can advance within the groove 115 and still remain within the channels 220 is if the inner tube 110 rotates to accommodate such movement of the pin 210. The helical nature of the groove causes such rotational movement of the inner tube 110.

It will be appreciated that the profile of the groove 115 can be varied and depending upon its precise characteristics, the movement of the inner tube 110 is controlled. For example, if it desired for the rotation of the inner tube 110 to be staged later in time, the length of the linear portion can be increased and therefore, the pin 210 does not enter into the helical portion as quickly as before and therefore, the rotation of the inner tube 110 is delayed.

Since the free end of the snare is fixed to the outer cannula 120, the result of the rotation of the inner tube 110 is that the coil of the snare tightens so that the cross-sectional area through the snare is approximately less than a third of the area when in the open configuration. It is also contemplated that any decrease, even a slight decrease, in the cross-sectional area of the snare will cause pressure on the biopsy piece. Therefore, the amount of rotation can be varied and there is no particular amount that is necessary for the proper functioning of the present invention.

With the tightening of the snare, there is a high probability that the biopsy piece will remain in the needle as the needle is removed. If the tightening of the snare does not immediately cause the biopsy piece to be cut, it will be significantly squeezed and/or notched, such that rearward motion of the needle, which causes rearward pressure on any biopsy piece proximal of the snare, will cause material proximal of the snare to detach from material that is distal of the snare.

The pin 210 advances forward until either (1) the pin 210 reaches the ends of the channels 220; (2) the pin 210 reaches the end of the helical portion; or (3) the pin 210 contacts the sleeve 160.

In the embodiment shown in FIG. 1, the flange 113 does not move axially relative to the inner tube 110 although it does move axially relative to the handle body 410. The flange members 177, 179 permit the inner tube 110 to rotate within the flange 113 and in addition, the flange 113 does not rotate relative to the handle body 410 since the flange 113 is constrained by the interaction of the lever 170 and the pin 180.

The present construction can therefore be thought of as a two stage mechanism in which the first stage is the firing of the actuator device 150 (first release of stored energy) to cause the sudden longitudinal advancement of the inner and outer tubes 110, 120 away from the handle body 410. This in turn causes the second pivotable lever 170 to disengage and there is a second firing of the second biasing element 190 which leads to the second stage where the inner tube 110 is rotated.

The operation of the snare 300 including the collection and removal of the soft tissue sample is preferably along the same lines as that which is disclosed in the patents disclosed hereinbefore.

The device can be reset using a sleeve and pin assembly as described previously. However, it is possible that the outer cannula flange 126 may not line up completely with the alignment sleeve 160 as the inner tube 110 and outer cannula 120 move backward into position and therefore, an additional mechanism might be required to compensate for this possibility. One such mechanism can include increasing the dimensions of the complementary portion (channel or groove 165) that accepts the flange 126 to allow the flange 126 to "find" its way into the grooves 165 and reset properly.

One will appreciate that the speed of needle transit into a specimen with significant internal structure does not have to be excessive since the internal structure provides stability and supports the shearing of the specimen by the needle. However, needle transit into tissue must be excessive for tissues with moderate or minimal internal structure in order that an appropriate shearing and tissue cutting force is developed. Moreover, not only shearing but transit of the specimen into the needle is facilitated by specimens with significant internal structure. Tissue with minimal internal structure does not support transit of the specimen into the needle as well and requires the needle to "move over" the specimen in a rapid fashion to facilitate specimen acquisition. The present design is one in which the needle, with stylet in place, can be brought to a certain position and the coring needle can then be rapidly advanced beyond the fixed position of the stylet. Accordingly, the present spring loaded mechanism projects the needle over the stylet in a matter of microseconds.

In sum, the pin and groove mechanism for rotating the snare coil has been developed to eliminate the need for an operator to rotate a lever to actuate the snare coil in applications where it is desirable to have a hand-held device that is spring-loaded and fired by pressing an activating button. Further, it coordinates the rapid axial projection of a needle with the requirement for a rotating movement to actuate the snare coil. The pin and groove mechanism can achieve these requirements through a number of different embodiments. In these embodiments, the pin moves along the groove and this can be achieved by either translating a sleeve axially relative to a pin that does not move axially or vice versa translating the pin (can be attached to a tubular structure) relative to a grooved sleeve that does not move in an axial position. In each of these configurations, one component (either the sleeve or pin) does not rotate, while the other component does rotate. The component that rotates is connected to the internal snare coil tubular member. In one embodiment, if the pin is fixed and does not rotate, axial movement of the sleeve causes the sleeve and any tube attached thereto (e.g., inner tube attached to snare coil) to rotate. In the second embodiment, if the sleeve does not rotate, that is, it is fixed in a nonrotatable position when it is translated along an axial direction, the pin will rotate and any tubular member connected to the pin, such as the internal snare coil cannula, will rotate as well.

It will be appreciated that the above described rotating needle construction is not limited to a needle having a snare coil design but rather a rotating needle construction can be provided for a simple coring needle. More specifically, a simple coring needle can incorporate the above rotational aspects by having a cannula with a grooved sleeve and pin mechanism to cause the cutting cannula to rotate as it is projected forward but does not include the inner tube with a snare coil coupled at one end thereof. The pin and groove mechanism thus can be used as a means for causing rotation of one cannula to another to cause this cutting (coring) cannula to rotate, thereby cutting the tissue for collection as opposed to actuating a snare coil (which is not present in this embodiment).

In an embodiment that incorporates the above first and second stages but does not include a snare, a simple rotating needle is provided and there is only a boring tube or cannula and sleeve 119 which is coupled thereto and the first biasing element 130. In this embodiment, there is no snare and the cutting action is derived from the rotation of the cannula 120 which is caused by the pin and groove mechanism 127, 123 that has been previously described. Thus, a simple rotating needle assembly is illustrated which is actuated using device 150.

It will also be understood that both the pin and groove mechanisms that are associated with the sleeve 119 in both of these embodiments can be modified so that the sleeve 119 has at least one pin formed as a part thereof and a groove is formed as part of the handle body and therefore, the rotating action is generated by the pin riding within the groove formed as part of the handle body.

Figure 13:
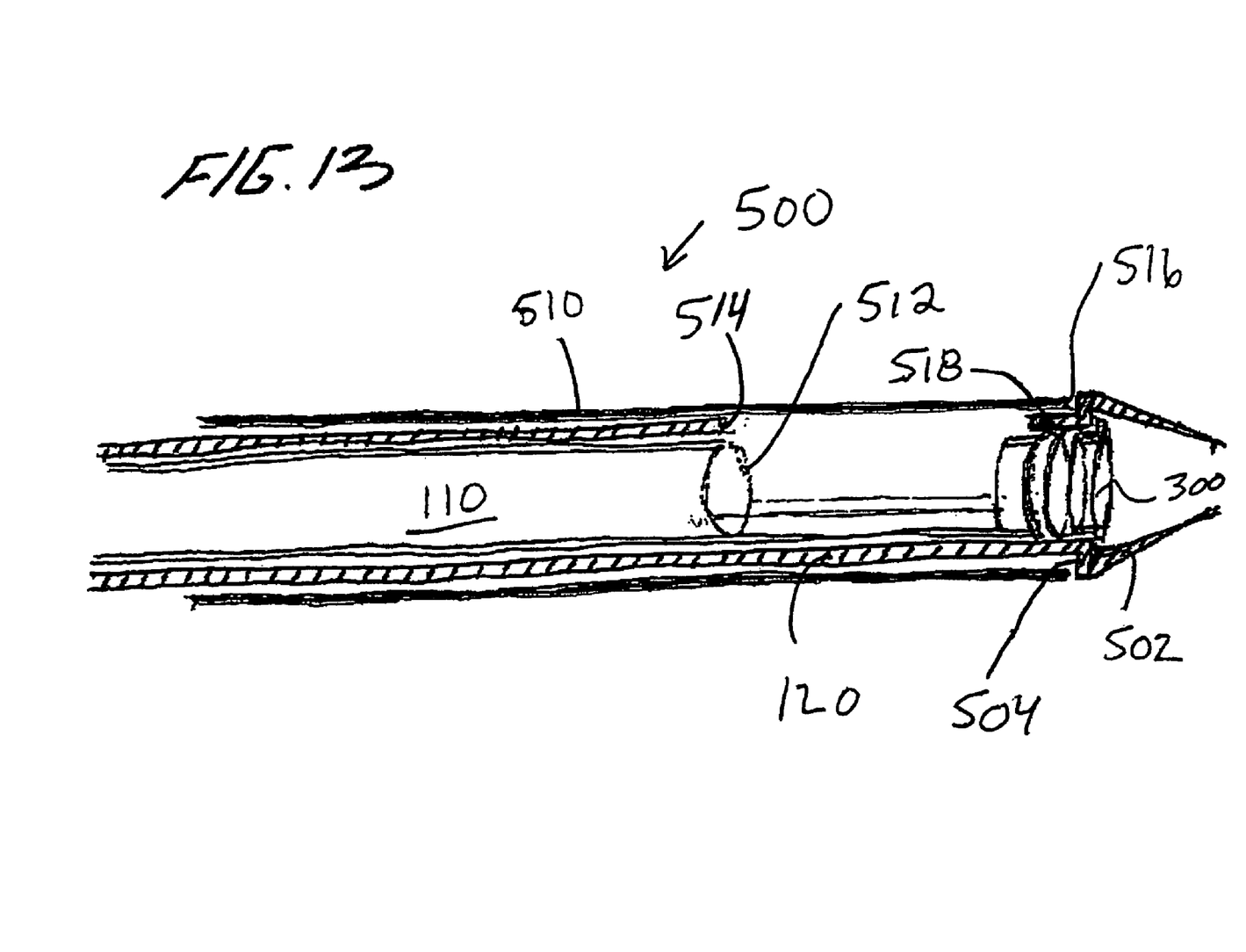
FIG. 13 is a partial perspective view of a biopsy needle having an internal window according to a second embodiment.

FIG. 13 illustrates yet another aspect of the present invention in which a three cannula biopsy needle 500 is provided. The needle 500 includes the inner tube 110, the outer cannula 120 and a retractable cannula 510. The construction of the inner tube 110 and outer cannula 120 and their operative cooperation with the snare 300 is similar to that disclosed in any of the above incorporated U.S. patents. The outer cannula 120 includes a cutting portion 502 formed at a distal end thereof and also includes a shoulder 504 that is defined by the cutting portion 502 and an elongated body of the outer cannula 120.

Each of the inner tube 110 and the outer cannula 120 includes a cut out or window formed therein. More specifically, the inner tube 110 includes a window 512 formed near but spaced from the distal end thereof. The window 512 is formed by removing a predetermined amount of the body of the inner tube 110 and in one embodiment, the window 512 is formed by removing between about 50% to 85% of the circumference of the body of the inner tube 110. For example, the window 512 can extend about 75% of the circumference of the inner tube 110. The distalmost section of the inner tube 110 is formed next to the window 512 and extends to the snare 300. Similarly, the outer tube 120 includes a cut out or window 514 that is formed near but spaced from the distal end thereof. The window 514 is formed by removing between about 50% and 85% of the circumference of the body of the outer cannula 120, e.g., removing about 75%. Preferably, the circumferential characteristics of the windows 512, 514 are complementary so that the two windows 512, 514 are in registration with respect to one another at select times.

More specifically, after the snare 300 has been actuated as disclosed in the above incorporated patents or in another manner and the inner tube 110 completes its rotation with respect to the outer cannula 120, the windows 512, 514 are preferably in complete registration with one another so that an individual outside of the outer cannula 120 can reach through the aligned windows 512, 514 and into the interior of the inner tube 100 to retrieve the collected specimen. Preferably, the windows 512, 514 are in complete registration with one another; however, the windows 512, 514 do not necessarily have to be perfectly aligned for the user to gain sufficient access therethrough to retrieve the collected specimen.

The retractable cannula 510 is complementary in size and shape to the other two cannulas so that the retractable cannula 510 slidably extends over the outer cannula 120. The retractable cannula 510 has a distal end 516 that abuts or nearly abuts the shoulder 504. A portion 518 of the outer cannula 120 adjacent the shoulder 504 serves as a platform or leading ledge so that the distal end of the retractable cannula 510 sits on the platform 518 when the retractable cannula 510 is in the fully extended position, whereby the windows 512, 514 are closed.

The retractable cannula 510 preferably extends into a handle body (not shown) and is operatively coupled thereto using conventional means so that it can be easily retracted along the outer cannula 120. For example, a biasing mechanism can be used to apply a biasing force against the retractable cannula 120 so that it remains in the fully extended position during normal operating conditions. In order to retract the retractable cannula 510 and expose the windows 512, 514, the user simply applies a force against the cannula 510 that overcomes the biasing force resulting in the retraction of the cannula 510 toward the handle body until the windows 512, 514 are exposed. It will be appreciated that the retractable cannula 510 can be locked in a retracted position using conventional releasable locking mechanisms so that the cannula 510 can remain locked out of the way of the windows 512, 514. For example, a releasable biased tab/detent type arrangement can be used.

It will be appreciated that in the present illustrated embodiment, the needle 500 is constructed of three cannulas each successively placed within the other. The middle cannula is the outer cannula 120 and it is thicker than the others since it provides for the majority of the strength and stability of the needle assembly. The snare 300 is attached to the innermost tube (inner tube 110) at its distal end. The inner tube 110 has the smallest thickness and as with the outer cannula 120, the cut away portion leaves the inner tube 110 with a cradle like appearance.

Since this embodiment includes a needle incorporating three cannulas, it is important to minimize the wall thickness of one of the cannulas and possibly two of them to minimize the diameter of the whole needle 500. It is possible that the inner tube 110 can be made of a durable thin plastic material with the snare 300 molded or lasered into the end of the inner tube 110. The retractable cannula 510 can be made of a thin medical grade stainless steel and the outer cannula 120 can be constructed of a thicker medical grade stainless steel. As the whole needle 500 represents a composite of three cannulas, the overall strength of the needle 500 with respect to its resistance towards bending is substantial.

In another embodiment, the most distal portion of the innermost tube 110 beyond the snare 300 can have a type of tab lock which could integrate with the needle tip of the outer cannula 120 to allow for a secure connection and rapid manufacturing.

Thus, in the embodiment shown in FIG. 13, the needle 500 incorporates a retracting part to facilitate recovery of a specimen that is contained within the inner tube 110.

It will be appreciated that the above described retractable needle construction is not limited to a needle having a snare coil design but rather a retractable needle construction can be provided for a simple coring needle. More specifically, a simple coring needle can be a two cannula needle with the inner cannula having a window cradle (a cut out as described above) and the outer cannula can operate as the retractable cannula. This embodiment does not incorporate a third snare coil cannula. It will also be appreciated that in this embodiment, the inner cannula can be designed to rotate as described above due to a pin and groove construction, while it still remains a coring needle without the provision of a snare coil.

In yet another embodiment, the present biasing mechanisms can be incorporated into a non-snarecoil rotating needle. In other words, this type of needle has a simple boring tube that has a biasing mechanism, such as the first biasing mechanism of FIG. 1, that causes the rapid axial advancement of the boring tube due to the release of energy that is stored in the first biasing element against the flange of the boring tube. The needle also has a rotating mechanism, such as the pin and groove arrangement of FIG. 1, that causes the rotation of the boring tube either concurrently with the axial advancement of the boring tube or after the boring tube has reached its end of axial travel. In this embodiment, there is no inner tube and no automatic active capture mechanism that results in actuation of a snarecoil since there is no snarecoil. As with the other previous embodiments, the rotating mechanism of the boring tube preferably includes one component, such as a pin or helical slot, that moves axially and another component, such as a helical slot or pin, that is axially steadfast. Either pin or the helical slot or even a helical ridge as described above can be associated with the boring tube, while the other complementary component is formed as part of the housing of the handle assembly.

Figure 12:
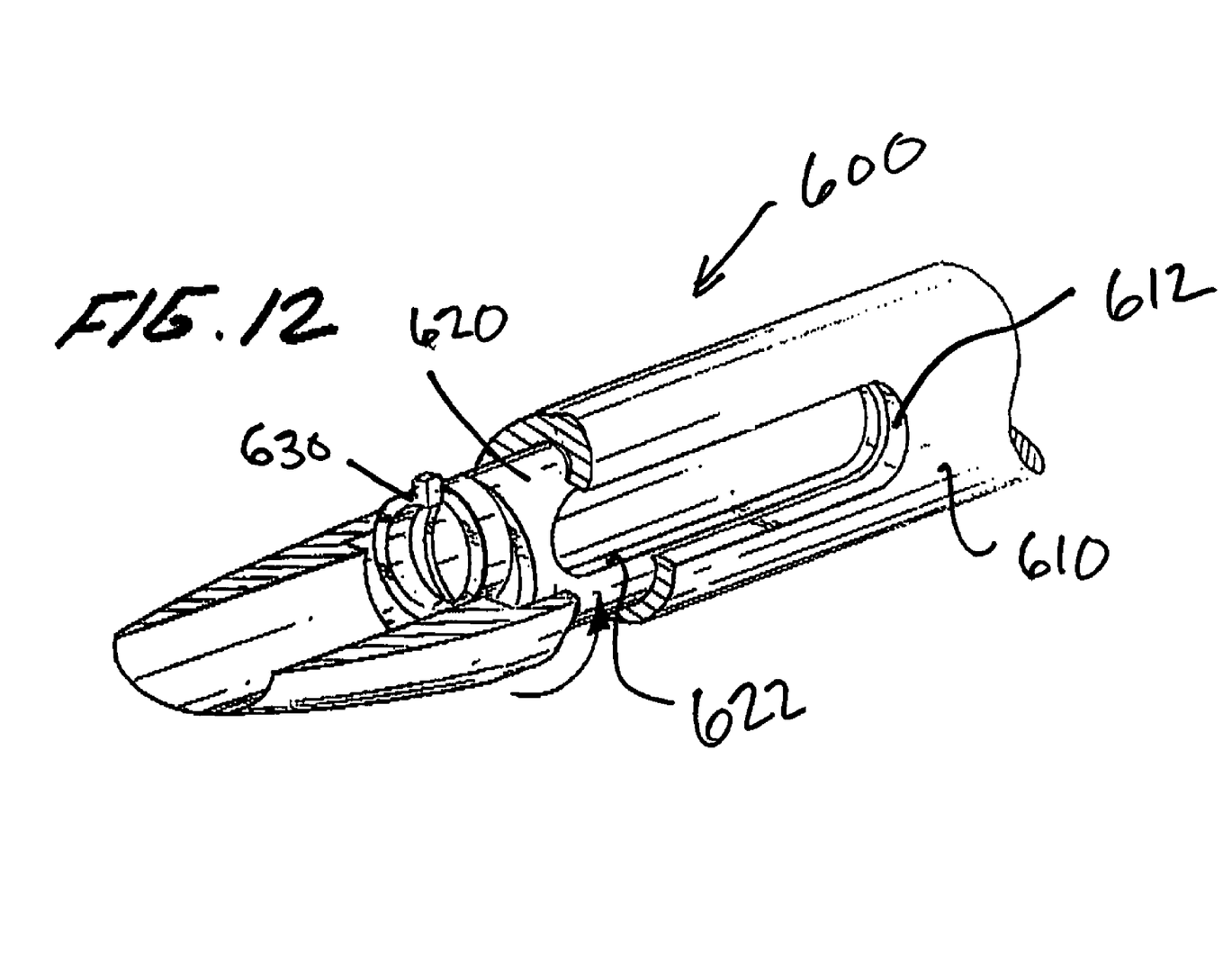
FIG. 12 is a partial perspective view of a biopsy needle having an internal window according to a first embodiment.

In yet another embodiment, shown in FIG. 12, a needle 600, such as the ones disclosed hereinbefore, includes an outer cannula 610 and an inner tube 620 that has or is connected to a snare 630 at a distal end thereof as previously described above and in the aforementioned patents. The outer cannula 610 includes a slot 612 that is formed therethrough to provide access into the interior of the outer cannula 610. For example, the slot 612 can have any number of different shapes and sizes so long as the slot 612 provides sufficient access into the interior of the outer cannula 610. The illustrated slot 612 is generally oblong shaped and is formed near the distal end of the outer cannula 610.

The inner tube 620 has a complementary slot 622 formed therein which is selectively axially aligned with slot 612 when the inner tube 622 is rotated within the outer cannula 610 to a position where the slots 612 and 622 at least partially overlap one another. The slot 622 extends completely through the inner tube 620 so as to permit the user to access the interior of the inner tube 620.

When the slots 612, 622 are aligned, a window is opened and permits the user to access the interior of the inner tube 620 from outside the outer cannula 610 by inserting an instrument through the side window into the interior of the inner tube 620 to access the specimen so that it can be removed through the window.

The inner tube 620 and the outer cannula 610 are arranged relative to the operable mechanisms of the needle such that when the inner tube 620 and outer cannula 610 are rapidly advanced forward the snarecoil 630 is actuated, the window defined by aligned slots 612, 622 remains closed. After the cutting/shearing action occurs, the snarecoil 630 is closed with the specimen being captured within the inner tube 620, the user then simply rotates the inner tube 620 so as to cause the inner slot 622 to become at least partially aligned with the outer slot 612, thereby opening the window and permitting easy removal of the specimen.

In addition, it will be appreciated that the window feature shown in FIG. 12 and the vacuum feature described below can be combined with any of the needle embodiments disclosed herein. For example, the window feature can be used in both snarecoil type needles and non-snarecoil type needles and can be used in needles that incorporate one or more of the mechanisms that either drive the needle axially forward or cause rotation of a part of the needle. Similarly, the window feature can be combined with the vacuum feature or the needle can include only one of these features and the vacuum feature similarly can be used in any of the above embodiments, including both snarecoil type needles and non-snarecoil type needles.

As previously mentioned, soft tissue specimens may not enter a needle as readily as specimens with more substantial internal structure because of issues of inadequate shearing/cutting and compromised specimen transit into the needle. One method of causing the specimens to more readily enter the needle is to create negative pressure (e.g., a vacuum condition) within the inner tube where the specimen is collected. Unfortunately, the existing needle constructions that have means for generating a negative pressure within the inner tube are very complex. For example, existing needle products include a cumbersome external vacuum device for generating the negative pressure.

Another way to generate a negative pressure internal to the needle is a means that takes advantage of the concept that when the needle is "thrown" forward over the stylet, the stylet is moving backward relative to the needle. As a result, the incorporation of a seal, such as a rubber O-ring or the like, between the stylet and the inner tube can generate a small but significant vacuum internal to the distal portion of the needle facilitating specimen transit into the needle. The vacuum is thus generated when the needle is "thrown" over the stylet and is cutting the tissue. For example, the needle can be "thrown" as a result of actuation of one of the aforementioned mechanisms.

The above feature of creating a negative pressure within the needle as it is fired can be the basis for a new biopsy technology. In one embodiment, a full core soft tissue needle projected forward and fired over a stylet that incorporates an air seal of some sort can generate enough internal negative pressure to not require the inclusion of a snarecoil in the needle to facilitate specimen recovery. Thus, in one embodiment, the snarecoil is removed and specimen recovery results from the application of a vacuum to the site.

In FIG. 2, the needle 100 is provided and includes inner tube 110 with the flange or the like 116 formed as a part thereof; the outer cannula 120 disposed around the inner tube 110; and the stylet 310. The stylet 310 has an outside diameter that is less than the diameter of the bore formed through the outer cannula 120 and therefore, there is a space or gap that is formed therebetween. In one embodiment, the flange 116 is an annular ring shapes member that extends outwardly from the inner tube 110. The outer cannula 120 also includes the flange or the like 126 that extends therearound.

A first seal element is disposed between the outer cannula and the inner tube 110. Any number of seal elements can be used, including but not limited to a rubber washer like member, an O-ring, a lubricant, or other sealant. A second seal element is disposed between the stylet 310 and the inner tube 110. As with the other embodiments, the second seal element can be in the form of a rubber ring, such an O-ring or it can be some other type of seal member or material. This second seal element that is disposed between the stylet 310 and the inner tube 110 acts as a positionably piston that generates the internal negative pressure in the needle, e.g., within the inner needle, to help draw the specimen by negative pressure into the inner tube 110. In other words, seal element allows the inner tube 110 and outer cannula 120 to act as a composite tube which the stylet 310 works against to generate the vacuum.

According to this aspect of the present invention, the soft tissue needle incorporates inner tube and outer cannula which are fired or rapidly projected forward over the stylet that has some material (second seal) disposed between the stylet and the inner tube that acts as an air seal. While the seal can be in the form of an O-ring, it can also be in the formed of some type of medically compatible polymer that sits between the inner tube and the stylet and it does not result in significant friction and seals the forward space from atmospheric pressure. This concept can also be applied to needles having a cumbersome external vacuum source, such as a Mammotome design from Ethicon Industries. In this type of embodiment, the outer cannula is not thrown forward rapidly but moves slowly as the inner circulating cutting blade cores out a specimen. In such a design, a shaft with an air sealing component remains steadfast as the outer needle is slowly projected forward thereby producing as distal internal vacuum and not requiring the external vacuum device to generate the force to facilitate specimen transit and retention in the needle.

It will be appreciated that the above described vacuum generating means can be employed in both a snarecoil design and a standard biopsy needle that does not include a snarecoil.

In yet another embodiment, a non-snarecoil rotating needle is provided and shares similar features as the needle of FIG. 1. In this embodiment, the needle has a simple boring tube that has the first stage rotation described above (e.g., cause by rotation of the sleeve 119) but does not include an inner tube and the second stage rotation, and thus the alignment sleeve 160 is eliminated also. In this embodiment, the boring tube advances axially due to actuation of mechanism 150 and as it axially advances, the interaction between elements 123, 127 causes rotation of the boring tube.

In another embodiment, a torque generating mechanism is provided and includes the second pivotable lever 170 and the second biasing element 190; however, the linear channels 220 and the ring shaped member 200 are eliminated. In this embodiment, an inner tube is provided and is similar to tube 110 with the exception that the helical groove is eliminated and replaced with one or more projections (bosses) that extend outwardly from an outer surface of the inner tube, preferably at a right angle thereto. If two projections are provided, they are preferably orientated 180 degrees apart. In this embodiment, the mechanism includes an axially driven helical sleeve that is disposed about the inner tube and includes one or more helical grooves or slots formed therein, similar to grooves 115 in FIG. 1. If there are two projections, then there are two slots. The sleeve also includes one or more, preferably two, guide fins or projections that ride within guide channels formed in the inner housing body 410 so as to prevent rotation of the sleeve as the sleeve travels axially within the housing.

The sleeve is contained in the housing body 410 and is permitted a degree of longitudinal axial travel therein. The sleeve includes a proximal end that has an opening or slot formed thereat with a distal end. The helical slot has an initial linear portion into which the projection is disposed and will travel in as the inner tube moves axially in the first stage due to the firing of the first biasing element 130 and movement of the outer tube 120 similar to FIG. 1. The slot of the sleeve is initially engaged and locked by the claw 174 of lever 170. As in FIG. 1, after a predetermined distance of axial travel, the lever 170 disengages from the sleeve, thereby causing the second biasing element 190 to release its energy against the flange to cause axial movement of the sleeve about the inner tube which does not move axially any more since the first stage is completed. It will be appreciated that once the sleeve is fired over the axially stationary inner tube, the engagement between the projections and the helical slots causes rotation of the inner tube and thereby causes activation of the snare. Once again, this embodiment shows an automatic active capture mechanism that is automatically fired after actuation of the first stage (longitudinal firing of the inner tube and the outer cannula 120) and at a predetermined time relative to the completion of the first stage.

After firing, the degree of axial travel of the sleeve can be restricted by a stop or the like, such as an object formed as part of the housing 410 and in any event, the travel of the sleeve will be limited by the presence of the flange 116. Once again, the guide channels prevent rotation of the axially advancing sleeve.

While exemplary drawings and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow, and equivalents thereof. In addition, the features of the different claims set forth below may be combined in various ways in further accordance with the present invention.

What is claimed is:

1. A biopsy needle for collecting a tissue specimen, the needle including an inner tube with a snare coil at a distal end thereof, an outer cannula, a stylet and a handle assembly that includes a first torque generating mechanism that imparts a selective and controlled torque action to the outer cannula relative to the handle assembly to cause actuation of a second torque generating mechanism that imparts a selective and controlled torque action to the inner tube relative to the outer cannula as the inner tube and outer cannula are advanced forward resulting in the snare coil at least partially closing, the first torque generating mechanism including a first component that is coupled to and associated with the outer cannula and a second component that is a part of a housing of the handle assembly, the needle further including an alignment sleeve that is disposed around a portion of the inner tube and the outer cannula, the alignment sleeve being received with a complementary groove formed in the housing so as to permit rotation of the alignment sleeve but restrict axial movement thereof, the alignment sleeve having guide channels formed therein to receive and control movement of the inner tube relative to the outer cannula such that in a first stage, both the inner tube and outer cannula move axially within the guide channels, while being prevented from rotating relative to one another and in a second stage, the inner tube is permitted to rotate relative to the outer cannula to cause actuation of the snare coil.

2. The needle of claim 1, wherein the second stage occurs after the inner tube and outer cannula are axially advanced, during the first stage, to a predetermined position where the outer cannula clears and becomes free of the guide channels of the alignment sleeve, whereby the outer cannula rotates relative to the inner tube.

3. The needle of claim 1, wherein the alignment sleeve contains a pair of guide channels formed about 180 degrees apart from one another, each groove extending the entire length of an inner surface of the alignment sleeve.

4. The needle of claim 2, wherein the outer cannula has a first flange formed as a part thereof, the first flange including a pair of first tabs and the inner tube has a second flange formed as a part thereof, the second flange including a pair of second tabs, one pair of first and second tabs being disposed in one guide channel, while a second pair of first and second tabs being disposed in the other guide channel, each of the first and second flanges having a locking lip that face one another for detachably locking the inner tube and the outer cannula to one another in the first stage.

5. The needle of claim 4, wherein the locking lips of the first and second flanges permit uniform rotation of the inner tube and the outer cannula such that the outer cannula and the inner tube remain in a locked position until the outer cannula becomes disengaged from the alignment sleeve and begins to rotate relative to the inner tube at which time the locking lip associated with the first flange becomes free and unlocked from the other locking lip of the second flange.

6. The needle of claim 1, wherein the first component comprises a first helical slot formed in the outer cannula and the second component comprises a first pin that is received in the first helical slot and is fixed to the housing of the handle assembly such that axial movement of the outer cannula in the first stage is translated to rotational movement thereof due to the first pin the first helical slot, whereby rotation of the outer cannula is translated to rotation of the alignment sleeve and the inner tube due to the outer cannula being coupled to both.

7. The needle of claim 1, wherein the first component comprises a first pin formed as part of the outer cannula and the second component comprises a first helical slot formed in the housing of the handle assembly, that receives the first pin, such that axial movement of the outer cannula in the first stage is translated to rotational movement thereof due to the first pin traveling in the first helical slot, whereby rotation of the outer cannula is translated to rotation of the alignment sleeve and the inner tube due to the outer cannula being coupled to both.

8. The needle of claim 1, wherein the second torque generating mechanism is constructed to automatically actuate at a predetermined point when the inner tube and outer cannula are axially advancing after activation of the first torque generating mechanism, the inner tube including one of a drive pin and a groove and a housing of the handle assembly including the other of the drive pin and groove such that as the inner tube and the outer cannula axially moves, the drive pin travels within the groove that is helically shaped so as to impart a rotation to the inner tube relative to the outer cannula as the drive pin travels within the helical groove.

9. The needle of claim 1, wherein the second torque generating mechanism includes:
 a second pivoting member that is pivotably coupled at a first end to a proximal end of the inner tube, with a second end including a claw, the second pivoting member includes a cam slot that receives a fixed pin that is fixed to the housing of the handle assembly such that as the inner tube and outer cannula move axially, the fixed pin travels within the cam surface causing a lifting of the second end;
 a retainer ring disposed about the inner tube and being engaged by the claw when the second biasing mechanism is in an energy storing position;
 a second biasing element disposed between the proximal end of the inner tube and the retainer ring and in a compressed state in the energy storing position; and
 wherein when the second torque generating mechanism is activated, the claw lifts off the retainer ring, thereby releasing the retainer ring and the second biasing element.

10. The needle of claim 9, wherein the drive pin contacts the retainer ring such that release of the retainer ring drives the drive pin within guide grooves that are formed in the handle assembly and contain the drive pin in a single plane, the stylet having an opening formed therethrough to accommodate the drive pin, wherein planar advancement of the drive pin in the guide slots and advancement of the drive pin in the helical groove is translated into rotation of the inner tube relative to the outer cannula.

11. The needle of claim 2, wherein the predetermined position occurs prior to the inner tube and the outer cannula reaching the end of their axial travel such that rotation is imparted to the inner tube as it axially advances.

12. The needle of claim 2, wherein the predetermined position occurs after the inner tube and the outer cannula reach ends of their axial travel.

13. The needle of claim 1, wherein the first torque generating mechanism also acts to rapidly advance the inner tube and the outer cannula beyond the stylet to provide a shearing action of the tissue specimen as at least the outer cannula is simultaneously rotated.

14. The needle of claim 13, wherein the inner tube and outer cannula are advanced over and beyond the stylet during both the first and second stages.

15. The needle of claim 1, wherein the first torque generating mechanism includes a first actuator operatively coupled to pivoting links that terminate in a claw at one end that engages a flange of the inner tube in an energy storing position so as to restrict axial movement of the inner tube and maintain the first biasing element in a compressed state.

16. The needle of claim 1, wherein the needle further includes:
 means for generating negative pressure within the needle for causing the specimen to more readily enter the needle, the means including a first seal and a second seal, the first seal being disposed between (a) a stylet that is slidably disposed within the inner tube and (b) the inner tube that generates a vacuum within a distal portion of the needle during axial travel of the inner tube and the outer cannula facilitating specimen transit into the needle, the second seal being disposed between the outer cannula and the inner tube.

17. The needle of claim 1, wherein the outer cannula has a first window formed therein and the inner tube having a second window which is selectively axially aligned with the first window when the inner tube is rotated within the outer cannula to a position where the windows at least partially overlap one another after the snare coil is tightened to permit access to the specimen collected in the needle at a location along a side of the needle spaced from a distal tip of the needle.

18. A biopsy needle for collecting a tissue specimen, the needle including an outer cannula, an inner tube received within the outer cannula and a stylet that is received within the inner tube, the inner tube having a snare coil at a distal end thereof, the outer cannula and the inner tube being coupled to one another by a linking feature that permits one of the outer cannula and inner tube to rotate relative to the other, the needle having a first actuation stage and a second actuation stage that is automatically activated as a result of activation of the first actuation stage, wherein during the first actuation stage, a first torque generating mechanism is actuated to drive the outer cannula in an axial longitudinal direction as well as causing rotation of the outer cannula as the outer cannula is driven, the needle further including an alignment sleeve that is axially fixed but rotatable and constructed to receive both the outer cannula and the inner tube such that the outer cannula and inner tube can freely travel axially within the alignment sleeve, wherein in the first stage, rotation of the outer cannula is translated to rotation of the alignment sleeve, and wherein in the second stage, the outer cannula is free of the alignment sleeve and the inner tube is rotated, as the inner tube remains axially steadfast, due to activation of a second biasing mechanism, whereby rotation of the inner tube is translated into rotation of the alignment sleeve and any rotation of the outer cannula is at a speed less than a speed of the inner tube such that the relative rotation between the outer cannula and the inner tube causes activation of the snare coil.

* * * * *